(12) United States Patent
Navab et al.

(10) Patent No.: US 10,448,860 B2
(45) Date of Patent: Oct. 22, 2019

(54) SYSTEM AND METHOD FOR BIOELECTRIC LOCALIZATION AND NAVIGATION OF INTERVENTIONAL MEDICAL DEVICES

(71) Applicant: The Johns Hopkins University, Baltimore, MD (US)

(72) Inventors: Nassir Navab, Munich (DE); Noah Cowan, Baltimore, MD (US); Bernhard Fuerst, Munich (DE); Eric S. Fortune, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1124 days.

(21) Appl. No.: 13/798,637

(22) Filed: Mar. 13, 2013

(65) Prior Publication Data

US 2014/0276190 A1 Sep. 18, 2014

(51) Int. Cl.
*A61B 34/20* (2016.01)
*A61B 5/06* (2006.01)

(52) U.S. Cl.
CPC .............. *A61B 5/068* (2013.01); *A61B 5/066* (2013.01); *A61B 34/20* (2016.02); *A61B 2034/2053* (2016.02)

(58) Field of Classification Search
CPC ............ A61B 5/065–066; A61B 5/068; A61B 2034/2053
See application file for complete search history.

(56) References Cited

U.S. PATENT DOCUMENTS

| 5,662,108 A | * | 9/1997 | Budd | A61B 5/04085 |
| | | | | 600/374 |
| 5,983,126 A | * | 11/1999 | Wittkampf | A61B 5/042 |
| | | | | 128/898 |
| 6,950,690 B1 | * | 9/2005 | Meron | A61B 1/00147 |
| | | | | 128/922 |
| 7,854,740 B2 | | 12/2010 | Carney | |

(Continued)

FOREIGN PATENT DOCUMENTS

EP 1421913 A1 5/2004

OTHER PUBLICATIONS

Betensky, et al., Use of a Novel Endoscopic Catheter for Direct Visualization and Ablation in an Ovine Model of Chronic Myocardial Infarction, Circulation, 2012, 126:2065-2072.

(Continued)

*Primary Examiner* — Devin B Henson
*Assistant Examiner* — Huong Q Nguyen
(74) *Attorney, Agent, or Firm* — BakerHostetler (57) ABSTRACT

A system and method for tracking a position of an interventional medical device configured to be deployed into a subject during a medical procedure. An anatomical dataset of the subject is acquired while at least one electrical sensor is disposed along the interventional medical device. A feedback signal is generated from the electrical sensor and is processed and analyzed to identify positional information of the interventional medical device. A position of the interventional medical device with respect to the anatomical dataset is identified and the position of the interventional (Continued)

medical device with respect to the anatomical dataset is shown on a display.

14 Claims, 4 Drawing Sheets

(56) References Cited

U.S. PATENT DOCUMENTS

| | | | | |
|---|---|---|---|---|
| 2004/0068204 | A1* | 4/2004 | Imran | A61B 1/00082 600/593 |
| 2011/0012594 | A1* | 1/2011 | Kimura | A61B 1/00016 324/309 |
| 2012/0158011 | A1* | 6/2012 | Sandhu | A61B 34/30 606/130 |
| 2013/0085416 | A1* | 4/2013 | Mest | A61B 5/042 600/587 |
| 2013/0293690 | A1* | 11/2013 | Olson | H04N 13/0438 348/56 |
| 2014/0005527 | A1* | 1/2014 | Nagarkar | A61B 5/05 600/424 |

OTHER PUBLICATIONS

Fricke, et al., The Electric Resistance and Capacity of Blood for Frequencies Between 800 and 4-1/2 Million Cycles, Journal of General Physiology, 1925, 9(2):153-167.
Geddes, et al., Specific Resistance of Blood at Body Temperature II, Medical and Biological Engineering, 1976, 14 (2):180-185.
Hill, et al., The Effect of Haematocrit on the Resistivity of Human Blood at 37C and 100 kHz, Medical and Biological Engineering, 1975, 13(2):182-186.
Hill, et al., The Importance of Blood Resistivity in the Measurement of Cardiac Output by the Thoracic Impedance Method, Medical and Biological Engineering, 1975, 13(2):187-191.
Mayekar, et al., Characterization of a Bionic Electrolocation Sensor Using Finite Element Modeling, IEEE Sensors, 2011, pp. 978-981.
Metzen, et al., A Biomimetic Active Electrolocation Sensor for Detection of Atherosclerotic Lesions in Blood Vessels, IEEE Sensors Journal, 2012, 12(2):325-331.
Roth, et al., Elektrische Fische and Elektrorezeption, Biologie in unserer Zeit, 1976, 6(1):11-21.
Solberg, et al., Robotic Electrolocation: Active Underwater Target Localization with Electric Fields, IEEE International Conference on Robotics and Automation, 2007, pp. 4879-4886.
Von Der Emde, et al., Electric Fish Measure Distance in the Dark, Nature, 1998, 395:890-894.
Von Der Emde, et al., Electric Fishes as Natural Models for Technical Sensor Systems, Proc. of SPIE, 2009, vol. 7365, pp. 73650B-1 thru 73650B-11.
Von Der Emde, Simulation of Bionic Electrolocation Sensor Based on Weakly Electric Fish, World Congress on Nature & Biologically Inspired Computing, 2009, pp. 830-834.

* cited by examiner

SYSTEM AND METHOD FOR BIOELECTRIC LOCALIZATION AND NAVIGATION OF INTERVENTIONAL MEDICAL DEVICES

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to systems and methods for tracking and navigating medical devices. More particularly, the invention relates to a method for tracking and navigating an interventional medical device while utilizing feedback signals generated by an array of electrical sensors on the interventional medical device.

In the medical arts, interventional medical devices, such as catheters or endoscopes, are frequently used to diagnose and treat various disorders in a patient, such as clogged or blocked blood vessels. An interventional medical device is introduced into a blood vessel of a patient by, for example, making an incision in the patient over the blood vessel and inserting the interventional medical device into the blood vessel of the patient. A interventional medical device operator such as a physician then maneuvers the interventional medical device through the blood vessels of the patient until the interventional medical device is properly situated to diagnose or treat the disorder. Similar techniques are used to insert interventional medical devices into other types of lumens within a patient.

In maneuvering the interventional medical device through the blood vessels or other lumens within the patient, there is a recurrent need to know the location of the interventional medical device within the body space of the patient. Conventional imaging systems create an image of the blood vessel or other lumen to provide 2- or 3-dimensional spatial relationships. If the position in three dimensions of the imaging head on the interventional medical device can be determined, then through use of three-dimensional imaging software, the relative positions and locations of the curves, twists, and turns, as well as the locations of the branch points, of the lumens can be determined. Knowing the positions allows a more accurate map of the patient to be created, which yields more effective diagnosis and treatment of the patient. For example, gathering accurate 3-D position data allows for an accurate blood flow map and consequent blood flow monitoring and modeling.

Traditionally, x-ray based technology, such as computed tomography (CT) has been used to provide a global roadmap of X-ray visible devices, showing their position within the patient. However, prolonged exposure to X-rays may be harmful to the patient, and it is therefore desirable to avoid such exposures.

In an effort to reduce radiation expose and not restrict access to the patient due to the patient being disposed within, for example, a CT gantry, 2-dimensional fluoroscopy is often used for interventional device tracking. Of course, 2-dimensional fluoroscopy suffers from a lack of information about the position of the device in a third dimension. To compensate for the lack of information in a third dimension, 2-dimensional fluoroscopy may be coupled with other tracking systems, such as magnetic tracking systems. Unfortunately, such systems are complex to implement because they require separate hardware, such as magnetic sensors associated with the interventional device and located at known positions external to the patient and, such systems must be coupled to the 2-dimensional fluoroscopy system to provide feedback in all three dimensions. At best, these systems are complex and can be inaccurate. Furthermore, they require repeated doses of ionizing radiation to update the 2-dimensional fluoroscopic data. Lastly, the device location must be registered with the anatomy, and magnetic trackers, for example, only provide absolute, and not relative position. Likewise, fluoroscopic images do not successfully image soft tissue, and so the registration system must rely heavily on preoperative data (e.g. from an angiogram) but anatomical features are prone to shift making this unreliable. Thus, these systems do not provide real-time feedback and require the continued exposure to ionizing radiation.

Thus, there is a need for a tracking system that can readily determine the location of a interventional medical device within a patient, relative to the relevant anatomy, without exposing the patient to harmful side effects, and that can be used with a wide variety of interventional medical devices or other imaging medical devices.

SUMMARY OF THE INVENTION

The present invention overcomes the aforementioned drawbacks by providing a system and method that tracks and navigates an interventional medical device during a medical procedure in real time. In particular, the present invention utilizes the generation of feedback signals generated by an array of electrodes on the interventional medical device. The feedback signals create an electric image of the local volume surrounding the interventional medical device In accordance with one aspect of the invention a system for tracking a position of an interventional medical device configured to be deployed into a subject during a medical procedure is disclosed. The system includes an interventional medical device configured to be deployed into a subject during a medical procedure. The system further includes at least one electrical sensor disposed along the interventional medical device to receive electrical signals available to the interventional medical device when deployed within the subject during the medical procedure and generate a feedback signal based on the received electrical signals. An anatomical dataset including anatomical information about the subject is stored on a non-transitive memory. The system includes a processor, communicatively coupled to the electrical sensor, which is configured to access the anatomical dataset from the non-transitive memory in order to receive the feedback signal from the electrical sensor and analyze the feedback signal to identify positional information of the interventional medical device relative to the anatomical dataset. The position of the interventional medical device with respect to the anatomical dataset is then communicated on a display coupled to the processor.

In accordance with another aspect of the invention, a method for tracking a placement of an interventional medical device deployed into a subject is disclosed. The method includes acquiring an anatomical dataset of the subject and providing an interventional medical device having at least one electrical sensor disposed along the interventional medical device. The interventional medical device is configured to be positioned within the subject during a medical procedure utilizing the interventional medical device. A feedback signal generated from the electrical sensor is then processed and analyzed to identify positional information of the interventional medical device. A position of the interventional medical device with respect to the anatomical dataset is identified and the position of the interventional medical device with respect to the anatomical dataset is then displayed.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
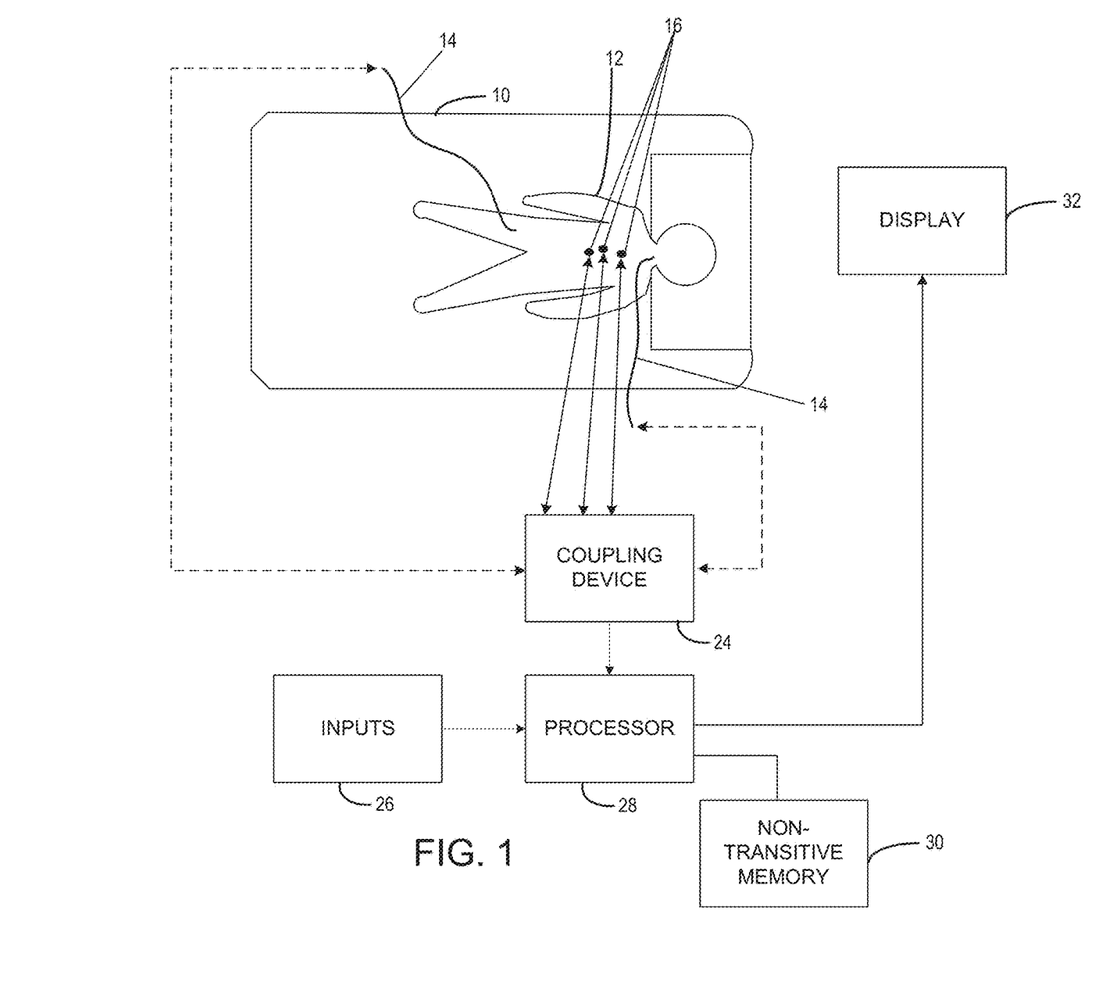
FIG. 1 is a block diagram of a system in accordance with the present invention.
Figure 2:
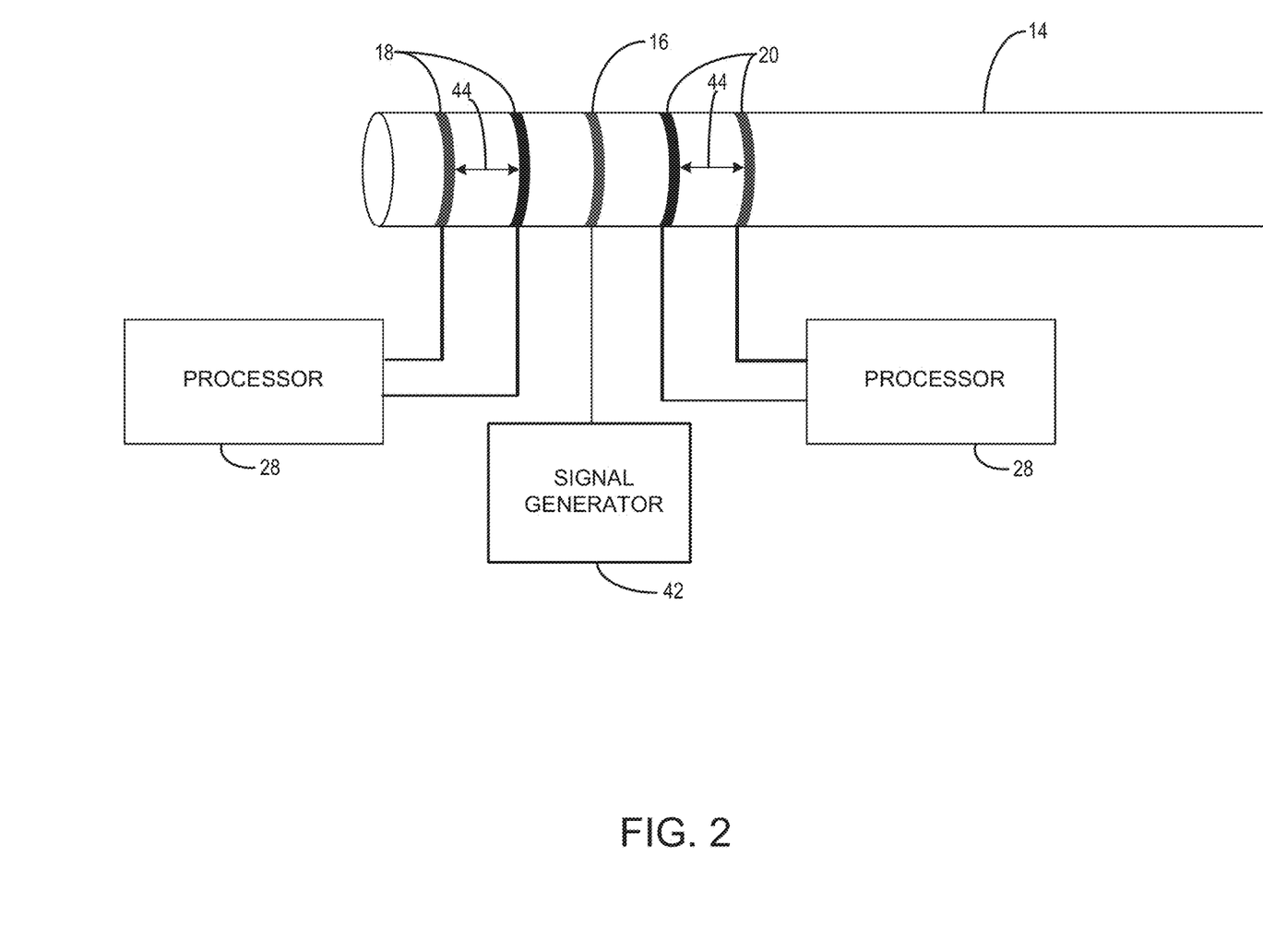
FIG. 2 is a block diagram of an interventional medical device with electrical sensors configured in accordance with the present invention.
Figure 4:
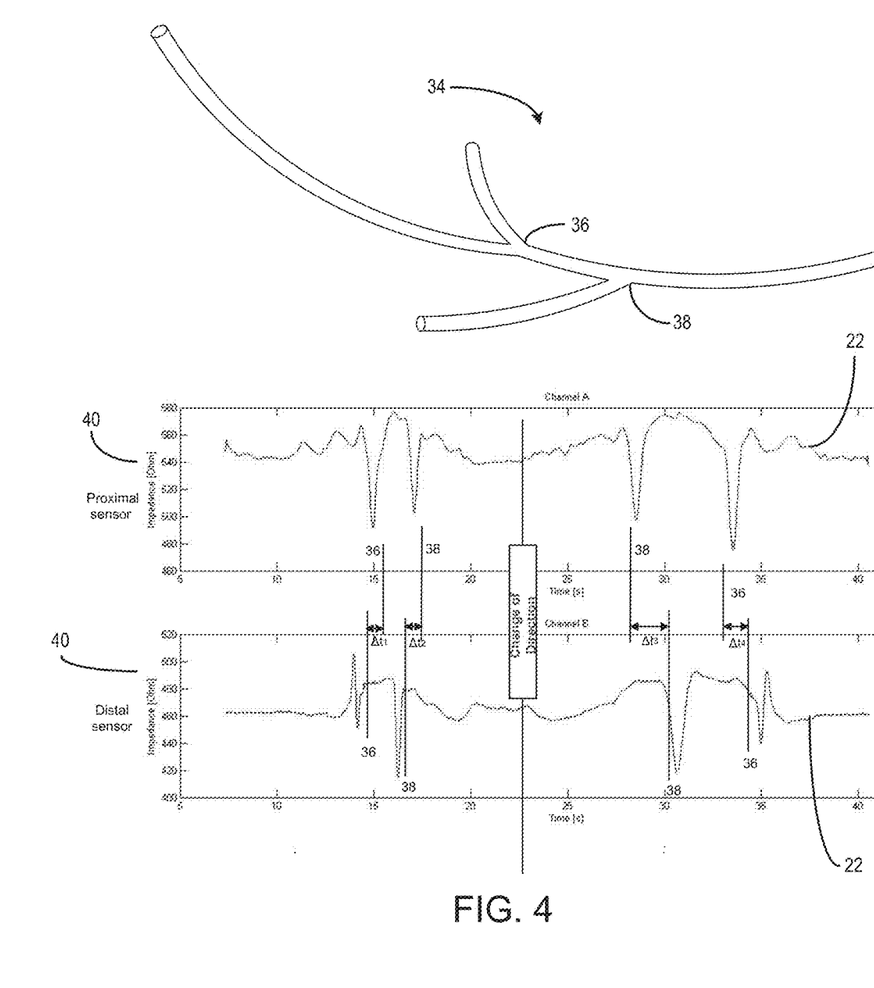
FIG. 4 is a schematic diagram of a vessel and corresponding impedance measurement over time as the interventional medical device is navigated through the vessel using the present invention.

Referring particularly now to FIG. 1, a subject 12 on a patient bed 10 with an interventional medical device 14 inserted into the femoral artery and the carotid artery is shown. Of course, these particular arteries or the use of vascular access points to locate the interventional medical device 14 is not limiting on the present invention. The interventional medical device 14 may be designed for a wide-variety of interventional procedures and access points. The interventional medical device 14 may be, for example, a catheter, laparoscope or endoscope. An electrical source 16 may be externally attached to the subject 12 or internally attached to the interventional medical device 14, or both as shown. The electrical source 16 can emit an electrical signal to be received by a distal electrical sensor 18 and a proximal electrical sensor 20 coupled to the interventional medical device 14, as shown in FIG. 2. The electrical source 16 may emit, for example, low-voltage, high-frequency signals. The distal electrical sensor 18 and the proximal electrical sensor 20 may be, for example, electrodes coupled to the interventional medical device 14. The distal electrical sensor 18 and the proximal electrical sensor 20 generate a feedback signal, for example, one non-limiting example of a feedback signal 22 is shown in FIG. 4, which is based on the received electrical signals emitted by the electrical source 16.

A coupling device 24 is configured to receive the feedback signal 22 from the distal electrical sensor 18 and the proximal electrical sensor 20 and transmit the feedback signal 22 to a processor 28. The processor 28 is communicatively coupled to the distal electrical sensor 18 and the proximal electrical sensor 20 to receive and measure the feedback signal 22. The processor 28 is configured to access a non-transitive memory 30 to receive an anatomical dataset, which includes anatomical information about the subject 12. The anatomical dataset may include, for example, a prior fluoroscopy, computed tomography (CT), magnetic resonance imaging (MRI), or other datasets, including models of the patient 12 or general anatomy of the patient 12. The anatomical dataset may be a previously-acquired dataset, or may be acquired contemporaneously with the medical procedure. Inputs 26 are provided to the processor 28 and can include patient demographics, a patient's previous medical history, and the like. A display 32 is also coupled to the processor 28 to communicate the position of the interventional device 14 with respect to the anatomical dataset.

Referring now to FIG. 2, an example of one configuration of the interventional medical device 14 is shown in further detail. As previously described, the distal electrical sensor 18 and the proximal electrical sensor 20 may be coupled to the interventional medical device 14. The distal electrical sensor 18 and the proximal electrical sensor 20 are spaced apart from one another a pre-determined distance 44 in order to identify positional information from the of the interventional medical device 14 during a medical procedure. The processor 28 is communicatively coupled to the distal electrical sensor 18 and the proximal electrical sensor 20. The electrical source 16 may be, for example, internal to the subject 12 and may be, for example, an electrical sensor coupled to the interventional medical device 14. The electrical source 16 is coupled to a signal generator 42 and configured to emit an electrical signal to be received by the distal electrical sensor 18 and the proximal electrical sensor 20.

Figure 3:
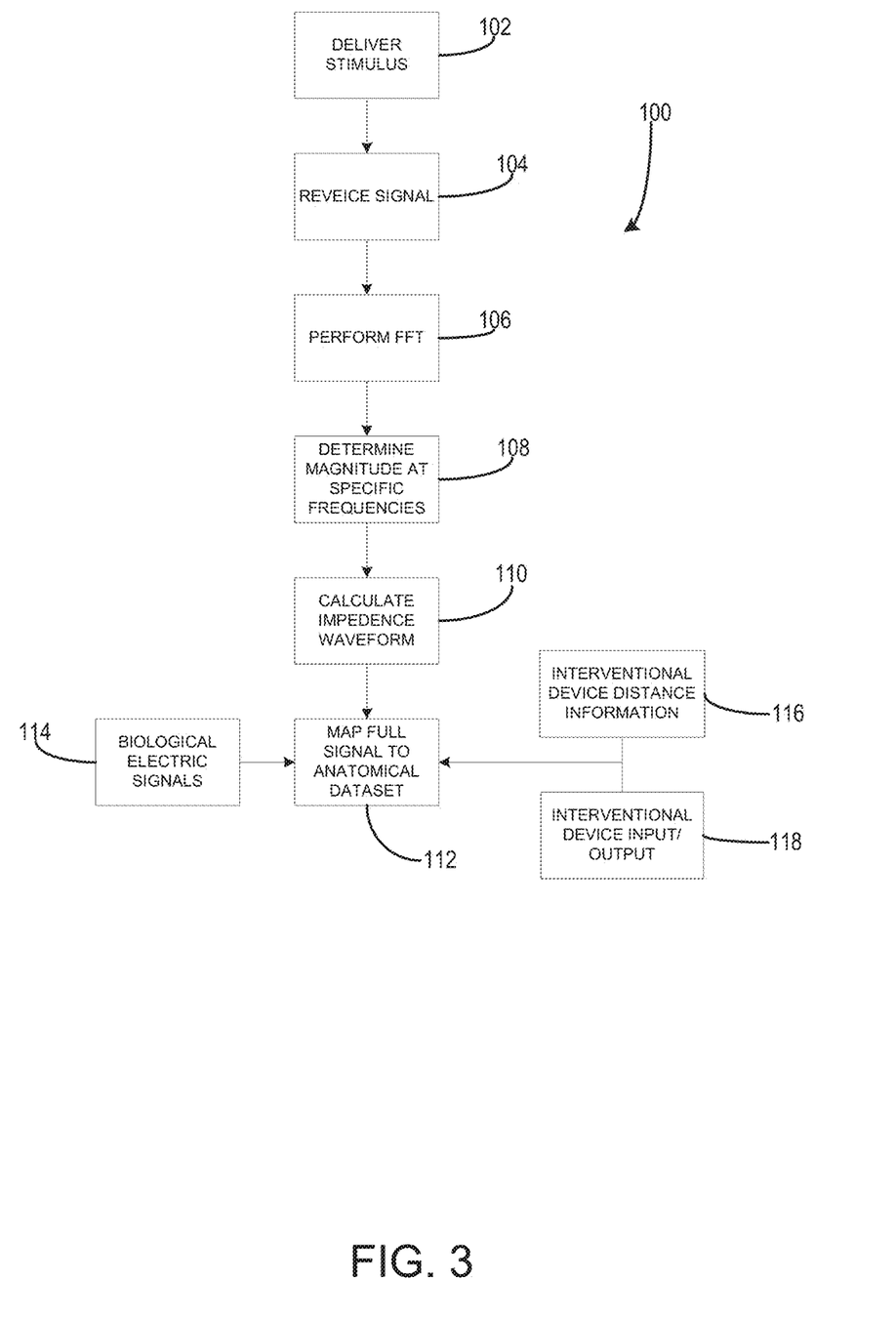
FIG. 3 is a flow chart setting forth the steps of processes for mapping a feedback signal to an anatomical dataset in accordance with the present invention.

Referring now to FIG. 3, a flow chart setting forth exemplary steps 100 for mapping a feedback signal 22 to an anatomical dataset is provided. To start the process, a stimulus is delivered at process block 102. The stimulus can be an electrical signal emitted by one or more electrical sources 16. The nature of the emitted electrical signal is not limited to a sinusoidal or periodic waveform, but may have a high signal-to-noise ratio. As described above, the electrical source 16 can be configured to emit an electrical signal from a location internal to the subject 12, from a location external to the subject 12, from other defined positions, or combinations of these options. If the electrical source 16 is configured to emit an electrical signal from a location external to the subject 12, the electrical signal propagates into the subject 12 to the distal and proximal electrical sensors 18, 20.

In one non-limiting example, the electrical source 16 may also be formed by external signal dischargers (ESD) attached to the subject 12 and configured to create a spatial varying signal overlay. During an inspection scan, the spatial varying signal overlay can be observed and mapped to anatomical or geometrical information acquired through the previously acquired anatomical dataset. Throughout the intervention, the ESD signal mix can then be mapped to the anatomical or geometrical data or other information, for example, to allow localization and navigation of the interventional medical device 14 based on pre-interventional imaging.

At process block 104 the distal electrical sensor 18 and the proximal electrical sensor 20 receive the electrical signal emitted from the electrical source 16. In response, the distal electrical sensor 18 and the proximal electrical sensor 20 generate the feedback signal 22 and send the feedback signal 22 to the processor 28. The feedback signal 22 indicates, for example, electric signals, which may include bio-electric signals, received by the distal electrical sensor 18 and the proximal electrical sensor 20 thereby creating an electric image of a local volume surrounding the interventional medical device 14. The local volume may be, for example, a vessel 34 as shown in FIG. 4. The processor 28 then performs a fast Fourier transform to the feedback signal 22 at process block 106 in order to analyze the feedback signal 22 and facilitate reduction of signal noise.

Once the fast Fourier transform is performed to the feedback signal 22, the magnitude of the feedback signal 22 may be determined at specific frequencies at process block 108. For example, the magnitude of the feedback signal 22 at, for example, frequencies below 5 kHz may be preferentially reviewed, due to ionization interferences at low frequencies. An impedance measurement 40 waveform of the feedback signal 22 may then be calculated at process block 110, as shown in FIG. 4, and mapped over time. The feedback signal 22 is mapped to anatomical images or models or other data sets at process block 112.

As illustrated in FIG. 4, the impedance measurement 40 waveform of the feedback signal 22 from both the proximal electrical sensor 20 and the distal electrical sensor 18 are shown. From the previously acquired anatomical dataset a reconstruction of the subject's 12 vessel 34 is provided. As the user navigates the interventional medical device 14 through the vessel 34, the interventional medical device 14 facilitates the transmission and simultaneous recording of the feedback signals 22 on the array of distal and proximal sensors 18, 20, giving rise to, for example, an electrical image. During the medical procedure, the feedback signals 22 are reconciled with the anatomical or other dataset, and the position of the interventional medical device 14 is displayed with respect to the other dataset on the display 32. Thus, the feedback signals 22 provide real-time feedback that does not require or use ionizing radiation and that can be readily coupled with other information, such as anatomical information about the patient, such as represented by images or models, to provide a real-time graphical indication of the position of the interventional device within the patient to the clinician. The graphical indication provide the user positional information and allows the guidance of interventional medical device 14.

More specifically, as the user navigates the interventional medical device 14 through the vessel 34, the impedance measurement 40 waveform of the feedback signal 22 from both the proximal electrical sensor 20 and the distal electrical sensor 18 can be mapped over time, as illustrated in FIG. 4. In the example at hand, when the interventional medical device 14 reaches a first bifurcation 36, or other topographical or anatomical waypoint, in the vessel 34 while the user is navigating the interventional medical device 14 in a first direction, a corresponding change in the impedance measurement 40 occurs. As shown in FIG. 4, the first bifurcation 36 occurs approximately at 14-15 seconds as indicated on the horizontal time axis, such that the distal electrical sensor 18 passes the first bifurcation 36 slightly before the proximal electrical sensor 20 passes the first bifurcation 36. Similarly, when the interventional medical device 14 reaches a second bifurcation 38, in the vessel 34 while the user is navigating the interventional medical device 14 in the first direction, a corresponding change in the impedance measurement 40 occurs. As shown in FIG. 4, the second bifurcation 38 occurs approximately at 16-17 seconds as indicated on the horizontal time axis, such that the distal electrical sensor 18 passes the second bifurcation 38 slightly before the proximal electrical sensor 20 passes the second bifurcation 38.

As the user retracts the interventional medical device 14, or moves the interventional medical device 14 in a second direction that is opposite the first direction, the interventional medical device 14 passes the second bifurcation 38 and the first bifurcation 36 in the vessel 34. Similar to movement in the first direction, corresponding changes in the impedance measurement 40 occurs while navigating the interventional medical device 14 in the second direction as shown in FIG. 4. The impedance measurement 40 waveform of the feedback signal 22 is illustrated a symmetrical signal in FIG. 4 as a result of the electrical source 16 being coupled to the interventional medical device 14. However, if the electrical source 16 is configured to emit an electrical signal from a location external to the subject 12, the electrical signal propagates into the subject 12 to the distal and proximal electrical sensors 18, 20, thereby creating a differential signal.

Of course, the above example of tracking bifurcations in a vascular lumen based on impedance measurements provides just one non-limiting example of an implementation in accordance with the present invention. For example, other processing analysis of the feedback signal may be performed to investigate parameters other than impedance. For example, in the above-described differential configuration, the signal differential from multiple sensors may be used to identify signal changes detected by the multiple sensors and be correlated with anatomical or topographical datasets, such as images or models or other maps against which the position of the interventional device can be tracked. For example, a change in the differential signal analysis may indicate that the interventional device is approaching a new anatomical structure, such as an organ or bone. Without tracking impedance or using images, this approach toward the anatomical structure may, for example, be illustrated on a model of the patient's anatomical structure. Thus, it is contemplated that the present invention may be embodied in many variations and the above-described implementation is but one non-limiting example.

Referring again to FIG. 3, the above-described process may be supplemented using other information sources. For example, by observing the biological electric signals at process block 114 and mapping the biological electric signals to spatial properties retrieved from the reference dataset at process block 112, the current position of the interventional medical device 14 can be determined at process block 112. Furthermore, at process block 116, distance information may be tracked and used to determine the position of the interventional medical device 14. Because the pre-determined distance 44 between the distal and proximal electrical sensors 18, 20 are known, the processor 28 can identify positional information of the interventional medical device 14 relative to the anatomical data set can be identified based on the impedance measurement 40. Additionally or alternatively, the lineal distance that the interventional medical device 14 is extended into the patient can be tracked at process block 118 and used in a similar manner. Once the positional information of the interventional medical device 14 is known, other metrics can be determined. For example, a velocity measurement can be computed based on a positional change and changes in time.

In summary, the present invention advantageously provides a system and method for tracking the navigation an interventional medical device during a medical procedure. In particular, the present invention acquires electrical information from sensors disposed on the interventional device and generates feedback signals based on the acquired electrical information. The feedback signals create an electric image of the local volume surrounding the interventional medical device that can be combined with anatomical information, such as maps or models, to display a location of the interventional device in real time.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for tracking a position of an interventional medical device configured to be deployed into a subject during a medical procedure, the system comprising:
   the interventional medical device configured to be deployed into the subject during the medical procedure, wherein the interventional medical device is configured to be displaced within the subject during the medical procedure;
   wherein an electrical source is disposed on or in the interventional medical device, and
   wherein the electrical source is configured to emit an electrical signal to a region of a body away from the interventional medical device being displaced within the subject during the medical procedure;
   wherein one or more electrical sensors is disposed on or in the interventional medical device, and
   wherein the one or more electrical sensors is configured to receive response electrical signals from the region of the body in response to the emitted electrical signal from the electrical source when the interventional medical device is displaced within the subject during the medical procedure to generate a feedback signal based on the received response electrical signals;
   a non-transitive memory configured to store therein an anatomical dataset including anatomical information that is specific to an anatomy of the subject;
   a processor configured to access the anatomical dataset from the non-transitive memory and communicatively coupled to the one or more electrical sensors to receive and analyze the feedback signal, based at least on the anatomical information that is specific to the anatomy of the subject, to identify positional information of the interventional medical device relative to the anatomical dataset and the anatomy of the subject during the displacement of the interventional medical device within the subject, wherein the positional information comprises a first position of the interventional medical device and a second position of the interventional medical device different from the first position and indicative of the displacement of the interventional medical device; and
   a display coupled to the processor to communicate at least the first position and the second position of the interventional medical device with respect to the anatomical dataset.

2. The system as recited in claim 1 wherein the feedback signal indicates bio-electric signals received by the one or more sensors.

3. The system as recited in claim 1 wherein the processor is further configured to determine at least one of a velocity and a positional change of the interventional medical device to identify the positional information of the interventional medical device.

4. The system as recited in claim 3, wherein the one or more electrical sensors comprises a plurality of electrical sensors disposed on or in the interventional medical device at a distal position to a proximal position and are configured to generate a plurality of feedback signals, wherein the processor is further configured to determine time delays reflected in the feedback signals in order to determine the velocity of the interventional medical device.

5. The system as recited in claim 1 wherein the interventional medical device is at least one of a catheter, guidewire, laparoscope or endoscope.

6. The system as recited in claim 1 wherein the anatomical dataset includes at least one of a prior fluoroscopy, computed tomography (CT), and magnetic resonance imaging (MRI) dataset.

7. The system as recited in claim 1 wherein the feedback signal is configured to create an electrical image of a local volume surrounding the interventional medical device.

8. A method for tracking a placement of an interventional medical device deployed into a subject, the method comprising the steps of:
   a) acquiring an anatomical dataset of that is specific to an anatomy of the subject;
   b) providing an interventional medical device having one or more electrical sensors disposed on or in the interventional medical device;
   c) positioning the interventional medical device within the subject during a medical procedure, wherein the interventional medical device is configured to be displaced within the subject during the medical procedure, wherein an electrical source is disposed on or in the interventional medical device and is configured to emit an electrical signal to a region of a body of the subject away from the interventional medical device being displaced within the subject during the medical procedure, and
   wherein the one or more electrical sensors disposed on or in the interventional medical device and is configured to receive a response electrical signal from the region of the body in response to the emitted electrical signal from the electrical source to generate a feedback signal based at least on the received response electrical signal;
   d) processing the feedback signal generated from the one or more electrical sensors;
   e) analyzing, based on the anatomical data set, the feedback signal to identify positional information of the interventional medical device relative to the anatomical data set and the anatomy of the subject during the displacement of the interventional medical device within the subject, wherein the positional information comprises a first position of the interventional medical device and a second position of the interventional medical device different from the first position and indicative of the displacement of the interventional medical device; and
   f) displaying at least the first position and the second position of the interventional medical device with respect to the anatomical dataset.

9. The method as recited in claim 8 wherein the anatomical dataset is a previously stored dataset acquired from a non-transitive memory.

10. The method as recited in claim 8 wherein feedback signal indicates bio-electric signals received by the one or more electrical sensors.

11. The method as recited in claim 8 further comprising processing at least one of a velocity and a positional change of the interventional medical device to identify the positional information of the interventional medical device.

12. The method as recited in claim 11, wherein the one or more electrical sensors comprise a plurality of electrical sensors generating a plurality of feedback signals, the plurality of electrical signals disposed on or in the interventional medical device at a distal position to a proximal position, and determining time delays reflected in the first and second feedback signals in order to determine the velocity of the interventional medical device.

13. The method as recited in claim 8 wherein the anatomical dataset includes at least one of a prior fluoroscopy, computed tomography (CT), and magnetic resonance imaging (MRI) dataset.

14. The method as recited in claim 8 wherein the interventional medical device is at least one of a catheter, guidewire, laparoscope or endoscope.

* * * * *